United States Patent
Ohashi et al.

(10) Patent No.: US 11,364,207 B2
(45) Date of Patent: Jun. 21, 2022

(54) PATCH AND PACKAGE THEREOF

(71) Applicant: HISAMITSU PHARMACEUTICAL CO., INC., Tosu (JP)

(72) Inventors: Hideaki Ohashi, Tsukuba (JP); Takito Shima, Tsukuba (JP); Kenji Ishigaki, Tsukuba (JP); Yasunari Michinaka, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

(21) Appl. No.: 16/483,511

(22) PCT Filed: Feb. 19, 2018

(86) PCT No.: PCT/JP2018/005786
§ 371 (c)(1),
(2) Date: Aug. 5, 2019

(87) PCT Pub. No.: WO2018/155390
PCT Pub. Date: Aug. 30, 2018

(65) Prior Publication Data
US 2020/0121611 A1  Apr. 23, 2020

(30) Foreign Application Priority Data
Feb. 24, 2017  (JP) .............. JP2017-034056

(51) Int. Cl.
*A61K 9/70* (2006.01)
*A61K 31/4045* (2006.01)
*A61K 47/02* (2006.01)

(52) U.S. Cl.
CPC ........ *A61K 9/7053* (2013.01); *A61K 31/4045* (2013.01); *A61K 47/02* (2013.01)

(58) Field of Classification Search
CPC ...... A61K 9/70; A61K 9/7007; A61K 9/7038; A61K 9/7053; A61K 9/1611; A61K 31/4045; A61K 47/02
See application file for complete search history.

(56) References Cited

U.S. PATENT DOCUMENTS

| | | | |
|---|---|---|---|
| 9,320,728 B2 * | 4/2016 | Yoshizaki | A61K 31/4045 |
| 2003/0124176 A1 * | 7/2003 | Hsu | A61K 31/4745 424/449 |
| 2004/0247656 A1 * | 12/2004 | Beier | A61K 9/7061 424/449 |
| 2011/0002976 A1 | 1/2011 | Yamamoto et al. | |
| 2011/0008398 A1 | 1/2011 | Morimoto et al. | |
| 2011/0028880 A1 | 2/2011 | Uchida et al. | |
| 2011/0195109 A1 | 8/2011 | Michinaka et al. | |
| 2012/0052113 A1 | 3/2012 | Uchida et al. | |
| 2014/0112974 A1 | 4/2014 | Takagi et al. | |
| 2014/0170205 A1 | 6/2014 | Uchida et al. | |
| 2015/0004215 A1 | 1/2015 | Yoshizaki et al. | |
| 2017/0056503 A1 * | 3/2017 | Hamamoto | A61K 47/02 |

FOREIGN PATENT DOCUMENTS

| | | |
|---|---|---|
| EP | 3342412 A1 | 7/2018 |
| JP | 2015-10066 A | 1/2015 |
| JP | 2015-151370 A | 8/2015 |
| WO | 2009/107478 A1 | 9/2009 |
| WO | 2009/107479 A1 | 9/2009 |
| WO | 2010/134433 A1 | 11/2010 |
| WO | 2012/165253 A1 | 12/2012 |
| WO | 2012/165254 A1 | 12/2012 |
| WO | 2017/018321 A1 | 2/2017 |
| WO | 2017/038768 A1 | 3/2017 |

OTHER PUBLICATIONS

International Search Report for PCT/JP2018/005786 dated Apr. 17, 2018 [PCT/ISA/210].
Communication dated Nov. 24, 2020 from the European Patent Office in application No. 18757059.3.

* cited by examiner

*Primary Examiner* — Lakshmi S Channavajjala
(74) *Attorney, Agent, or Firm* — Sughrue Mion, PLLC

(57) ABSTRACT

A patch comprising:
a backing layer; and
an adhesive layer, wherein
the adhesive layer contains a mixture of a pharmaceutically acceptable acid addition salt of ropinirole and potassium hydrogen carbonate, and
the mixture contains at least one selected from the group consisting of ropinirole and pharmaceutically acceptable acid addition salts thereof and potassium hydrogen carbonate.

4 Claims, No Drawings

PATCH AND PACKAGE THEREOF

CROSS REFERENCE TO RELATED APPLICATIONS

This application is a National Stage of International Application No. PCT/JP2018/005786 filed Feb. 19, 2018, claiming priority based on Japanese Patent Application No. 2017-034056 filed Feb. 24, 2017.

TECHNICAL FIELD

The present invention relates to a patch, and more particularly to a patch and a package thereof, the patch containing ropinirole and/or a pharmaceutically acceptable salt thereof.

BACKGROUND ART

Ropinirole is known as a drug useful for the treatment of Parkinson's disease, restless leg syndrome, and the like, and studies have been conducted in recent years on transdermal administration of preparations containing ropinirole and/or a pharmaceutically acceptable salt thereof from the viewpoints of reduction of administration frequency, compliance improvement, ease of administration and discontinuation thereof, and so on.

For example, International Publication No. 2010/134433 (PTL 1) describes a transdermal absorption preparation which includes a support and an adhesive layer containing ropinirole or a pharmaceutically acceptable acid addition salt thereof, and International Publication No. 2012/165253 (PTL 2) and International Publication No. 2012/165254 (PTL 3) each describe a ropinirole-containing patch which includes a backing layer and an adhesive layer containing ropinirole and/or a pharmaceutically acceptable salt thereof. Moreover, these PTLs 1 to 3 mention sodium hydroxide and the like as a desalting agent for a pharmaceutically acceptable acid addition salt (acid adduct) of ropinirole.

Additionally, International Publication No. 2009/107478 (PTL 4) and International Publication No. 2009/107479 (PTL 5) each describe a patch including a support and an adhesive layer, in which the adhesive layer contains ropinirole and a metal salt produced by the reaction between an acid addition salt of ropinirole with a desalting agent. Furthermore, these PTLs 4 and 5 also mention sodium hydroxide and the like as the desalting agent.

What is more, Japanese Unexamined Patent Application Publication No. 2015-10066 (PTL 6) describes a method for manufacturing a patch containing ropinirole, in which an adhesive layer composition containing a specific amount of a ropinirole free form is heated and cooled under specific conditions to enable suppression of crystal precipitation of the ropinirole free form for a long period of time.

CITATION LIST

Patent Literature

[PTL 1] International Publication No. 2010/134433
[PTL 2] International Publication No. 2012/165253
[PTL 3] International Publication No. 2012/165254
[PTL 4] International Publication No. 2009/107478
[PTL 5] International Publication No. 2009/107479
[PTL 6] Japanese Unexamined Patent Application Publication No. 2015-10066

SUMMARY OF INVENTION

Technical Problem

The present inventors have found that a patch having an adhesive layer obtained by using a mixture of an acid addition salt of ropinirole and a desalting agent as described in PTLs 1 to 5 is excellent in skin permeability of ropinirole but, albeit rarely, may undergo precipitation with time of crystals in the adhesive layer after a long period of time following manufacture (for example, 20 days or more), which means that a better long term storage stability is required. Note that the present inventors have also found that the crystals precipitated in this case are mainly the crystals of ropinirole free form generated when the acid addition salt of ropinirole is desalted by the desalting agent.

The present invention has been made in view of the above problem of the conventional art, and an object thereof is to provide a patch which is excellent in skin permeability of ropinirole and which sufficiently suppresses crystal precipitation in the adhesive layer for a long period of time, and a package thereof.

Solution to Problem

The present inventors have made earnest studies to achieve the above object, and found as a result that the crystal precipitation is sufficiently suppressed even after the passage of a long period of time following manufacture by using a patch including a backing layer and an adhesive layer, in which, as a patch containing at least one selected from the group consisting of ropinirole and pharmaceutically acceptable salts thereof, the adhesive layer contains a mixture of a pharmaceutically acceptable acid addition salt of ropinirole and potassium hydrogen carbonate, that is, a composition containing at least one selected from the group consisting of ropinirole and pharmaceutically acceptable acid addition salts thereof and potassium hydrogen carbonate. In addition, the present inventors have found that such a suppression effect is exhibited if a specific manufacturing method as described in PTL 6 is not applied.

Moreover, while strong bases such as sodium hydroxide have been used as desalting agents for pharmaceutically acceptable acid addition salts of ropinirole, the present inventors have found that the patch obtained by using a pharmaceutically acceptable acid addition salt of ropinirole and potassium hydrogen carbonate is excellent in skin permeability of ropinirole in spite of the fact that potassium hydrogen carbonate is a weak base. This led to the completion of the present invention.

Specifically, a patch of the present invention is a patch comprising:
a backing layer; and
an adhesive layer, wherein
the adhesive layer contains a mixture of a pharmaceutically acceptable acid addition salt of ropinirole and potassium hydrogen carbonate, and
the mixture contains at least one selected from the group consisting of ropinirole and pharmaceutically acceptable acid addition salts thereof and potassium hydrogen carbonate.

In the patch of the present invention, the mixture preferably further contains a potassium hydrogen carbonate-derived component. In addition, in the patch of the present invention, a content of the potassium hydrogen carbonate and/or the potassium hydrogen carbonate-derived component in terms of potassium hydrogen carbonate is 0.5 to 3.0 moles relative to a content of 1.0 mole of the ropinirole and/or the pharmaceutically acceptable acid addition salt thereof in terms of ropinirole free form.

Moreover, in the patch of the present invention, a content of the ropinirole and/or the pharmaceutically acceptable acid addition salt thereof in terms of ropinirole free form is 7.7 to 20.0% by mass relative to a total mass of the adhesive layer. Furthermore, a package of the present invention comprises the patch of the present invention enclosed in a packaging container.

Advantageous Effects of Invention

The present invention makes it possible to provide a patch which is excellent in skin permeability of ropinirole and which sufficiently suppresses crystal precipitation in the adhesive layer for a long period of time, and a package thereof.

DESCRIPTION OF EMBODIMENTS

Hereinafter, the present invention is described in detail with reference to its preferable embodiments.

A patch of the present invention is a patch comprising a backing layer and an adhesive layer, wherein
the adhesive layer contains a mixture of a pharmaceutically acceptable acid addition salt of ropinirole and potassium hydrogen carbonate, and
the mixture contains at least one selected from the group consisting of ropinirole and pharmaceutically acceptable acid addition salts thereof and potassium hydrogen carbonate.

The patch of the present invention includes a backing layer and an adhesive layer. The backing layer is not particularly limited as long as it can support the adhesive layer to be described later, and a known one as the backing layer of a patch can be employed as appropriate. Examples of the material of the backing layer according to the present invention include polyolefins such as polyethylene and polypropylene; ethylene-vinyl acetate copolymers, vinyl acetate-vinyl chloride copolymers, polyvinyl chlorides, and the like; polyamides such as nylon; polyesters such as polyethylene terephthalate (PET), polybutylene terephthalate, and polyethylene naphthalate; cellulose derivatives; and synthetic resins such as polyurethane, and metals such as aluminum. Among these, polyesters and polyethylene terephthalate are preferable from the viewpoints of the non-adsorbability for the drug and the non-transmittability for the drug. Example forms of the backing layer include sheet-type products such as films, sheets, sheet-shaped porous bodies, and sheet-shaped foams; fabrics such as woven fabric, knitted fabric (knit), and nonwoven fabric; foil; and laminates of these. In addition, although the thickness of the backing layer is not particularly limited, it is preferably in a range of 5 to 1000 µm from the viewpoints of ease of manufacturing and ease of operation when applying the patch.

The patch of the present invention may further include a release liner on a surface of the adhesive layer opposite to the backing layer. Examples of the release liner include films and sheets made of polyolefins such as polyethylene and polypropylene; ethylene-vinyl acetate copolymers, vinyl acetate-vinyl chloride copolymers, polyvinyl chlorides, and the like; polyamides such as nylon; polyesters such as polyethylene terephthalate; cellulose derivatives; and synthetic resins such as polyurethane, and aluminum and paper, and laminates thereof. These release liners are preferably ones which have been subjected to release treatment such as coating with a silicone-containing compound or coating with a fluorine-containing compound on the surface in contact with the adhesive layer for the purpose of facilitating peeling from the adhesive layer.

The adhesive layer according to the present invention contains a mixture of a pharmaceutically acceptable acid addition salt of ropinirole and potassium hydrogen carbonate.

In the present invention, examples of the acid of the pharmaceutically acceptable acid addition salt of ropinirole include hydrochloric acid, sulfuric acid, nitric acid, phosphoric acid, phosphorous acid, hydrobromic acid, maleic acid, malic acid, ascorbic acid, tartaric acid, lauric acid, stearic acid, palmitic acid, oleic acid, myristic acid, lauryl sulfuric acid, linolenic acid, and fumaric acid.

In the mixture, the desalting reaction (neutralization reaction) between the pharmaceutically acceptable acid addition salt of ropinirole and potassium hydrogen carbonate can produce ropinirole (free form, hereinafter referred to as the "ropinirole free form" in some cases) from the pharmaceutically acceptable acid addition salt of ropinirole. Therefore, the mixture according to the present invention contains potassium hydrogen carbonate as well as at least one of a ropinirole free form, which is a reaction product between the pharmaceutically acceptable acid addition salt of ropinirole and potassium hydrogen carbonate, and the pharmaceutically acceptable acid addition salt of ropinirole remaining unreacted. The ropinirole free form may be a product formed into a free form during manufacture of the patch or may be a product formed into a free form in the patch after manufacture, and may be one of these or a mixture of two or more thereof. The mixture according to the present invention preferably contains at least the ropinirole free form and potassium hydrogen carbonate from the viewpoints of better skin permeability of ropinirole and suppression of crystal precipitation in the adhesive layer for a longer period of time.

In addition, in the mixture according to the present invention, the desalting reaction (neutralization reaction) between the pharmaceutically acceptable acid addition salt of ropinirole and potassium hydrogen carbonate can produce a component derived from potassium hydrogen carbonate, that is, a potassium hydrogen carbonate-derived component as a reaction product between the pharmaceutically acceptable acid addition salt of ropinirole and potassium hydrogen carbonate. Therefore, mixture according to the present invention may further contain the potassium hydrogen carbonate-derived component. Note that the potassium hydrogen carbonate-derived component contained may be a reaction product generated by the reaction between potassium hydrogen carbonate and an acid other than the pharmaceutically acceptable acid addition salt of ropinirole (an acid of a component that may be contained, if necessary, in the adhesive layer (such as an organic acid or an inorganic acid), which is described later).

Examples of the potassium hydrogen carbonate-derived component include carbon dioxide gas ($CO_2$), carbonate ions ($CO_3^{2-}$), hydrogen carbonate ions ($HCO_3^-$), potassium ions ($K^+$), and potassium salts, and may be one of these or a mixture of two or more thereof. Although it depends on the type of the pharmaceutically acceptable acid addition salt of ropinirole or the acid that may be contained, if necessary, in the adhesive layer described above, examples of the potassium salt include potassium chloride, potassium sulfate, potassium nitrate, potassium phosphate, potassium phosphite, potassium bromide, potassium maleate, potassium malate, potassium ascorbate, potassium tartrate, potassium laurate, potassium stearate, potassium palmitate, potassium oleate, potassium myristate, potassium lauryl sulfate, potassium linolenate, potassium fumarate, potassium carbonate, potassium pyrosulfite, potassium iodide, dipotassium phosphate, potassium dihydrogen phosphate, potassium hydroxide, potassium acetate, potassium hydrogen tartrate, and potassium thiocyanate. When the mixture according to the present invention further contains the potassium hydrogen carbonate-derived component, the potassium hydrogen carbonate-derived component preferably contains at least one of the potassium salts.

In the adhesive layer according to the present invention, the content of the ropinirole and/or a pharmaceutically acceptable acid addition salt thereof (the content of the ropinirole free form or the content of the pharmaceutically acceptable acid addition salt of ropinirole, or their total content in the case of containing both the ropinirole free form and the pharmaceutically acceptable acid addition salt of ropinirole) is, in terms of ropinirole free form, preferably 7.7 to 20% by mass, more preferably 7.7 to 17.6% by mass, further preferably 7.7 to 13.5% by mass or 8.8 to 17.6% by mass, even more preferably 8.8 to 13.2% by mass, and particularly preferably 9.0 to 13.2% by mass relative to the total mass of the adhesive layer. When the content of the ropinirole and/or a pharmaceutically acceptable acid addition salt thereof is less than the lower limit, the skin permeability of ropinirole tends to be decreased. On the other hand, when the upper limit is exceeded, the effect of suppressing the precipitation of crystals in the adhesive layer is decreased and the absolute amount in the adhesive layer is increased, which tends to make it difficult to extend the adhesive layer composition during the formation of the adhesive layer and to obtain a uniform preparation.

In the adhesive layer according to the present invention, the content of the potassium hydrogen carbonate and/or the potassium hydrogen carbonate-derived component (the content of the potassium hydrogen carbonate or, in the case of containing both the potassium hydrogen carbonate and the potassium hydrogen carbonate-derived component, their total content), that is, the amount of potassium hydrogen carbonate blended during manufacture of the patch is, in terms of potassium hydrogen carbonate, preferably 0.5 to 3.0, more preferably 0.7 to 3.0 moles, further preferably 1.0 to 3.0 moles, and even more preferably 1.0 to 2.5 moles relative to a content of 1.0 mole of the ropinirole and/or a pharmaceutically acceptable acid addition salt thereof in terms of ropinirole free form. When the content of the potassium hydrogen carbonate and/or the potassium hydrogen carbonate-derived component is less than the lower limit, there is a tendency that the effect of suppressing the precipitation of crystals in the adhesive layer is decreased and the skin permeability of ropinirole is decreased. On the other hand, when the upper limit is exceeded, the absolute amount in the adhesive layer is increased, which tends to make it difficult to extend the adhesive layer composition during the formation of the adhesive layer and to obtain a uniform preparation.

In addition, in the adhesive layer according to the present invention, the content of the potassium hydrogen carbonate and/or the potassium hydrogen carbonate-derived component relative to the total mass of the adhesive layer preferably satisfies the conditions for the molar ratio to the content of the ropinirole and/or a pharmaceutically acceptable acid addition salt thereof in terms of ropinirole free form and is, although it cannot be said unconditionally due also to the dependence on that content, preferably 1.5 to 21.0% by mass, more preferably 1.5 to 16.0% by mass, further preferably 3.0 to 16.0% by mass, and even more preferably 3.5 to 15.0% by mass in terms of potassium hydrogen carbonate. When the content of the potassium hydrogen carbonate and/or the potassium hydrogen carbonate-derived component is less than the lower limit, its amount relative to the content of the ropinirole and/or a pharmaceutically acceptable acid addition salt thereof is small, which results in a tendency that the effect of suppressing the precipitation of crystals in the adhesive layer is decreased and the skin permeability of ropinirole is decreased. On the other hand, when the upper limit is exceeded, it tends to be difficult to extend the adhesive layer composition during the formation of the adhesive layer and to obtain a uniform preparation.

The adhesive layer of the patch generally contains an adhesive. In the present invention, examples of the adhesive include rubber-based adhesives, acrylic adhesives, and silicone-based adhesives. These may be used singly or two or more kinds thereof may be used in combination. Although not particularly limited, the adhesive contained in the adhesive layer according to the present invention preferably contains at least one selected from the group consisting of rubber-based adhesives and silicone-based adhesives and more preferably contains at least a rubber-based adhesive from the viewpoints of strong cohesion and suppression of plasticizing action of the ropinirole free form on the adhesive.

Examples of the rubber-based adhesive include a natural rubber and a synthetic rubber. Among these, at least one selected from the group consisting of synthetic rubbers not having hydroxyl groups or carboxyl groups, such as styrene-isoprene-styrene block copolymers (SIS), isoprene rubbers, polyisobutylene (PIB), styrene-butadiene-styrene block copolymers (SBS), styrene-butadiene rubbers (SBR), and polybutene, is more preferable from the viewpoint that it is possible to sufficiently suppress the production of related substances of ropinirole in the adhesive layer.

When the rubber-based adhesive is contained, the content thereof is preferably 10 to 89.7% by mass and more preferably 15 to 87.5% by mass relative to the total mass of the adhesive layer. When the content of the rubber-based adhesive is less than the lower limit, the cohesion of the adhesive layer tends to be decreased. On the other hand, when the upper limit is exceeded, the adhesive layer tends to be so hard that the adhesion of the patch is decreased.

In the case of using the acrylic adhesive, examples of the acrylic adhesive include acrylic acid•acrylic acid octyl ester copolymers, 2-ethylhexyl acrylate•vinylpyrrolidone copolymers, acrylic acid ester•vinyl acetate copolymers, 2-ethylhexyl acrylate•2-ethylhexyl methacrylate•dodecyl methacrylate copolymers, methyl acrylate•2-ethylhexyl acrylate copolymer resins, and acrylic polymers contained in acrylic resin alkanolamine solution, all of which are listed as adhesives in "Japanese Pharmaceutical Excipients Directory 2016 (edited by the International Pharmaceutical Excipients Council Japan)."Among these, it is preferable to use commercially available DURO-TAK acrylic adhesive series (manufactured by Henkel), EUDRAGIT series (manufactured by Evonik), and the like.

In the case of using the silicone-based adhesive, it is preferable to use a polymer having an organopolysiloxane skeleton as the silicone-based adhesive. When the polymer having an organopolysiloxane skeleton has hydroxyl groups (for example, silanol groups), at least one of the hydroxyl groups is preferably capped with a trimethylsilyl group. In addition, the polymer having an organopolysiloxane skeleton further preferably has adhesion. Note that the capping by a trimethylsilyl group includes the end-capping of the terminal silanol group of the polymer having an organopolysiloxane skeleton with a trimethylsilyl group. Examples of such a polymer having an organopolysiloxane skeleton include polydimethylsiloxane (such as a polymer denoted by MQ in the representation according to ASTMD-1418), polymethylvinylsiloxane (such as a polymer denoted by VMQ in the representation according to ASTMD-1418), and polymethylphenylsiloxane (a polymer denoted by PVMQ in the representation according to ASTMD-1418).

In the case of using the acrylic adhesive and/or the silicone-based adhesive, the content thereof (total content in the case of a mixture) is preferably 10 to 89.7% by mass and further preferably 15 to 80% by mass relative to the total mass of the adhesive layer from the viewpoint of excellence in formability of the adhesive layer and skin permeability of active ingredients.

As long as the effects of the present invention are not impaired, the adhesive layer according to the present invention may further contain a drug other than ropinirole and a pharmaceutically acceptable salt thereof; an absorption enhancer (transdermal absorption enhancer); and an additive such as an adsorbent, a tackifier, a plasticizer, a solubilizer for the drug, a filler, a stabilizer, or a preservative, and the like.

Examples of the drug other than ropinirole and a pharmaceutically acceptable salt thereof include nonsteroidal anti-inflammatory analgesics (such as diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, methyl salicylate, glycol salicylate, valdecoxib, celecoxib, rofecoxib, and amfenac), antihistamines (such as diphenhydramine, chlorpheniramine, mequitazine, and homochlorcyclizine), antihypertensives (such as diltiazem, nicardipine, nilvadipine, metoprolol, bisoprolol, and trandolapril), antiparkinsonians (such as pergolide, bromocriptine, and selegiline), bronchodilators (such as tulobuterol, isoproterenol, and salbutamol), antiallergics (such as ketotifen, loratadine, azelastine, terfenadine, cetirizine, and acitazanolast), local anesthetics (such as lidocaine and dibucaine), anesthetic analgesics (such as morphine), agents for urinary organs (such as oxybutynin and tamsulosin), psychoneurotic agents (such as promazine and chlorpromazine), steroid hormone drugs (such as estradiol, progesterone, norethisterone, cortisone, and hydrocortisone), antidepressants (such as sertraline, fluoxetine, paroxetine, and citalopram), antidementia drugs (such as donepezil, rivastigmine, galantamine), antipsychotics (such as risperidone and olanzapine), central nervous system stimulants (such as methylphenidate), osteoporosis treatment drugs (such as raloxifene and alendronate), breast cancer prevention drugs (such as tamoxifen), anti-obesity drugs (such as mazindol and sibutramine), insomnia remedies (such as melatonin), antirheumatics (such as actarit), and pharmaceutically acceptable salts thereof. These may be used singly or two or more kinds thereof may be used in combination.

Examples of the absorption enhancer include isopropyl myristate, isopropyl palmitate, lauryl alcohol, hexyl laurate, myristyl alcohol, oleyl alcohol, isostearyl alcohol, octyldodecanol, benzyl alcohol, glycerin monooleate (GMO), propylene glycol monolaurate (PGML), polyoxyethylene sorbitan monooleate (Tween 80), polyoxyethylene sorbitan tristearate (Tween 65), polyoxyethylene sorbitan monostearate (Tween 60), polyoxyethylene sorbitan monolaurate (Tween 20), and lauric acid diethanolamide (LADA), these may be used singly or two or more kinds thereof may be used in combination.

Examples of the adsorbent include inorganic and/or organic substances having hygroscopicity, and more specific examples thereof include minerals such as talc, kaolin, and bentonite; silicon compounds such as fumed silica (such as Aerosil (registered trademark)) and hydrated silica; metal compounds such as zinc oxide and dried aluminum hydroxide gel; weak acids such as lactic acid and acetic acid; saccharides such as dextrin; and high molecular polymers such as polyvinylpyrrolidones, aminoalkyl methacrylate copolymers, crospovidone, carboxyvinyl polymers, and butyl methacrylate methyl methacrylate copolymers. These may be used singly or two or more kinds thereof may be used in combination.

The tackifier is blended mainly for the purpose of enhancing the adhesion of the adhesive base. Examples of such a tackifier include rosin-based resins, terpene-based resins, petroleum-based resins (such as alicyclic saturated hydrocarbon resins), phenol-based resins, and xylene-based resins. These may be used singly or two or more kinds thereof may be used in combination. When such a tackifier is further contained in the adhesive layer, the content thereof is more preferably 10 to 79.7% by mass and further preferably 15 to 70% by mass relative to the total mass of the adhesive layer from the viewpoint of improving the adhesive force of the adhesive layer and/or reducing the local irritation at the time of peeling off.

The plasticizer is blended mainly for the purpose of adjusting the adhesive properties of the adhesive layer, the flow characteristics in the manufacture of the adhesive layer, the transdermal absorption characteristics of the drug, and the like. Examples of such a plasticizer include silicone oils; petroleum-based oils such as paraffinic process oils, naphthenic process oils, and aromatic process oils; squalane and squalene; vegetable-based oils such as olive oil, camellia oil, castor oil, tall oil, and peanut oil, dibasic esters such as dibutyl phthalate and dioctyl phthalate; liquid rubbers such as polybutene and liquid isoprene rubber; and diethylene glycol, polyethylene glycol, propylene glycol, and dipropylene glycol. These may be used singly or two or more kinds thereof may be used in combination. Among these, silicone oils, liquid paraffin, and liquid polybutene are preferable as the plasticizer. When such a plasticizer is further contained in the adhesive layer, the content thereof is more preferably 5 to 60% by mass and further preferably 5 to 50% by mass relative to the total mass of the adhesive layer from the viewpoint of a better adhesive force as a patch.

The solubilizer is blended mainly for the purpose of promoting dissolution of the drug. Examples of such a solubilizer include organic acids such as acetic acid, aliphatic alcohols, and surfactants. These may be used singly or two or more kinds thereof may be used in combination. Among these, organic acids and aliphatic alcohols are preferable as the solubilizer.

The filler is blended mainly for the purpose of adjusting the adhesive force of the adhesive layer. Examples of such a filler include aluminum hydroxide, calcium carbonate, and magnesium carbonate; silicates such as aluminum silicate and magnesium silicate; and silicic acid, barium sulfate, calcium sulfate, calcium zincate, zinc oxide, and titanium oxide. These may be used singly or two or more kinds thereof may be used in combination.

The thickness of the adhesive layer according to the present invention is not particularly limited, and an example thereof is such a thickness that the mass per unit area of the adhesive layer is 25 to 250 g/m².

The patch of the present invention is preferably packaged (preferably enclosed) in a packaging container after manufacture until the time of use from the viewpoint that it is possible to further effectively suppress crystal precipitation of ropinirole. The packaging container is not particularly limited, and it is possible to appropriately use one usually usable as the packaging container of a patch. It is preferable to use, for example, a plastic packaging bag, a plastic packaging bag having a metal layer (for example, an aluminum layer) formed therein, a metal packaging bag (for example, an aluminum packaging bag), or the like.

The package of the present invention, which has the patch of the present invention enclosed in the packaging container, more preferably further includes an oxygen scavenging means. Examples of the oxygen scavenging means include oxygen scavengers using iron powder and oxygen scavengers containing vitamin C as a main component, enclosed in the packaging container (more specifically, the AGELESS series (manufactured by Mitsubishi Gas Chemical Company, Inc.), the PharmaKeep series (manufactured by Mitsubishi Gas Chemical Company, Inc.), and the like); and the packaging container including a layer with an oxygen scavenging function (more specifically, a layer mixed with powder of aluminum, zinc, manganese, copper, iron, hydrosulfite, activated carbon, and the like).

The patch of the present invention can be manufactured by, for example, the following manufacturing method. First, the pharmaceutically acceptable acid addition salt of ropinirole, potassium hydrogen carbonate, the adhesive and, if necessary, another drug, the absorption enhancer, the additive, a solvent, and the like are mixed in accordance with a conventional method to obtain a uniform adhesive layer composition. Examples of the solvent include anhydrous ethanol, toluene, hexane, ethyl acetate, cyclohexane, heptane, butyl acetate, ethanol, methanol, xylene, and isopropanol. Next, this adhesive layer composition is applied on the surface (usually on one surface) of the backing layer. Then, if necessary, the solvent is removed by drying to form an adhesive layer, followed by, if necessary, further cutting into a desired shape to obtain the patch of the present invention. The method for manufacturing the patch of the present invention may heat, but does not particularly have to heat, the adhesive layer composition.

In addition, the method for manufacturing the patch of the present invention may further include the step of bonding the release liner on a surface of the adhesive layer opposite to the backing layer, in which the patch of the present invention is obtained by first forming an adhesive layer by applying the adhesive layer composition on one surface of the release liner, then bonding the backing layer on a surface of the adhesive layer opposite to the release liner, and, if necessary, cutting the resultant into a predetermined shape. Moreover, if necessary, the obtained patch may be enclosed in the packaging container to form the package of the present invention.

EXAMPLES

Hereinafter, the present invention is described more specifically based on Examples and Comparative Examples, but the present invention is not limited to the following Examples. Note that the patches obtained in Examples and Comparative Examples were subjected to a skin permeation test, a crystal precipitation evaluation test, and a preparation suitability evaluation test in the following methods.

<Skin Permeation Test ((In Vitro) Hairless Mouse Skin Permeation Test)>

First, the skin of the trunk of a hairless mouse was peeled off, and the fat was removed from the skin. Then, a patch which had been subjected to cutting into a size of 2.5 cm² and removal of the release liner was applied to the epidermis side of the skin. This was set in a Franz permeation test cell of a flow-through type such that the dermis side came into contact with a receptor solution, and the cell was filled with the receptor solution (PBS). Subsequently, the receptor solution was fed at a flow rate of approximately 2.5 mL/hr while circulating a circulation water, which had been warmed such that the receptor solution was kept at a temperature of 32° C., around the outer periphery. Then, the receptor solution was collected or every 4 hours for 24 hours. The concentration of ropinirole (ropinirole free form) in the collected receptor solution was measured by high performance liquid chromatography to obtain the accumulated skin permeation amount 24 hours after the start of application as the 24-hr accumulated skin permeation amount ($\mu g/cm^2$). In addition, the 24-hr accumulated skin permeation amount of the patch for reference (patch obtained in Comparative Example 1 to be described later) was set to 100 to calculate the relative value of the 24-hr accumulated skin permeation amount of each patch, which was defined as the relative accumulated permeation rate (%). Note that each test was carried out on three patches, and the results were for their average values.

<Crystal Precipitation Evaluation Test>

First prepared were three patches each cut into a size of 6.25 cm², and each of them was enclosed in an aluminum packaging bag containing a desiccant (manufactured by Sud-CHEMIE, trade name "Sorb-It"), followed by storage for 21 days at 4° C. The surface of the adhesive layer of each patch after 21-day storage was visually observed, and crystal precipitation in the adhesive layer was evaluated in accordance with the following criteria:

A: No crystal precipitation was observed;
B: Crystal precipitation was observed partially; and
C: Crystal precipitation was observed entirely.

<Preparation Suitability Evaluation Test>

For each patch, the release liner was peeled off from the adhesive layer to observe the peeling state between the adhesive layer and the release liner, and the preparation suitability was evaluated in accordance with the following criteria:

A: The adhesive layer and the release liner were smoothly peeled off, leaving no problem as a preparation;
B: Part of the adhesive layer remained on the release liner due to cohesive failure of the adhesive layer, leaving a problem as a preparation; and
C: The adhesive layer and the backing layer were peeled off due to anchoring failure between the adhesive layer and the backing layer, leaving a problem as a preparation.

Example 1

First, 10 parts by mass of ropinirole hydrochloride, 10.11 parts by mass of potassium hydrogen carbonate (which corresponds to 3.0 moles relative to a number of moles of 1.0 mole of ropinirole hydrochloride in terms of ropinirole free form), and 79.89 parts by mass of rubber-based adhesive base composition were added to an appropriate amount of solvent (anhydrous ethanol and toluene), followed by mixing to obtain an adhesive layer composition. The rubber-based adhesive base composition used was a mixture of 100 parts by mass of styrene-isoprene-styrene block copolymer, 200 parts by mass of aliphatic saturated hydrocarbon resin, and 80 parts by mass of liquid paraffin. Next, the obtained adhesive layer composition was applied on a release liner (polyethylene terephthalate film subjected to release treatment) to a thickness of 100 g/m$^2$, and the solvent was removed by drying to form an adhesive layer. A backing layer (polyethylene terephthalate film) was stacked on the surface of the obtained adhesive layer opposite to the release liner to obtain a patch stacked in the order of backing layer/adhesive layer/release liner.

Examples 2 to 14

The patches were obtained in the same manner as that of Example 1 except that the compositions of the adhesive layer compositions were the compositions shown in Tables 3 and 5 to 7 below.

Comparative Examples 1 to 13

The patches were obtained in the same manner as that of Example 1 except that potassium hydrogen carbonate was replaced with sodium hydroxide, sodium hydrogen carbonate, sodium lactate, and potassium hydroxide in accordance with the compositions listed in Tables 1, 2, 4, and 7, and the compositions of the adhesive layer compositions were the compositions shown in the tables.

The patches obtained in Examples and Comparative Examples were subjected to the skin permeation test, the crystal precipitation evaluation test, and the preparation suitability evaluation test described above. Table 1 shows the results (24-hr accumulated skin permeation amount) obtained by carrying out the skin permeation test on the patches obtained in Comparative Example 1 to 5 and Example 1 together with the compositions of the adhesive layer compositions (excluding the solvent). Note that in the tables below, the numerical value in the parentheses within the entry of ropinirole hydrochloride indicates parts by mass in terms of ropinirole free form, and the numerical value in the parentheses within the entry of sodium hydroxide, sodium hydrogen carbonate, sodium lactate, or potassium hydroxide indicates the number of moles thereof relative to a number of moles of 1.0 mole of ropinirole acid addition salt in terms of ropinirole free form.

TABLE 1

|  | Comparative Example 1 | Comparative Example 2 | Comparative Example 3 | Comparative Example 4 | Comparative Example 5 | Example 1 |
|---|---|---|---|---|---|---|
| Adhesive Layer Composition [Parts by Mass] | | | | | | |
| Ropinirole Hydrochloride | 10 | 10 | 10 | 10 | 10 | 10 |
| (In Terms of Free Form) | (8.8) | (8.8) | (8.8) | (8.8) | (8.8) | (8.8) |
| Sodium Hydroxide | 1.08 | — | — | — | — | — |
| (Mol/Ropinirole Free Form) | (0.8) | | | | | |
| Sodium Hydrogen Carbonate | — | 2.83 | 8.49 | — | — | — |
| (Mol/Ropinirole Free Form) | | (1.0) | (3.0) | | | |
| Sodium Lactate | — | — | — | (3.79) | 11.36 | — |
| (Mol/Ropinirole Free Form) | | | | (1.0) | (3.0) | |
| Potassium Hydrogen Carbonate | — | — | — | — | — | 10.11 |
| (Mol/Ropinirole Free Form) | | | | | | (3.0) |
| Rubber-Based Adhesive Base Composition | 88.92 | 87.17 | 81.51 | 86.21 | 78.64 | 79.89 |
| Total | 100 | 100 | 100 | 100 | 100 | 100 |
| Skin Permeability | | | | | | |
| 24-hr Accumulated Skin Permeation Amount [μg/cm$^2$] | 374 | 325 | 374 | 56 | 11 | 465 |

As is clear from the results shown in Table 1, the patch of the present invention obtained by using potassium hydrogen carbonate (Example 1) was confirmed to have a sufficiently large 24-hr accumulated skin permeation amount and an excellent skin permeability as in the case of using sodium hydroxide, which has conventionally been used as a desalting agent (Comparative Example 1). Note that the same results were confirmed when the skin permeation test was also carried out on the patch obtained in the same manner as that of Example 1 except that the rubber-based adhesive base composition was replaced with a silicone-based adhesive. On the other hand, the 24-hr accumulated skin permeation amount was confirmed to be significantly low in the case of using sodium lactate (Comparative Examples 4 and 5).

Next, Table 2 and 3 show the results (relative accumulated permeation rate based on the 24-hr accumulated skin permeation amount of the patch obtained in Comparative Example 1) obtained by carrying out the skin permeation test on the patches obtained in Comparative Example 2 and 6 to 9 and Examples 2 to 6 together with the compositions of the adhesive layer compositions (excluding the solvent).

TABLE 2

|  | Comparative Example 1 | Comparative Example 6 | Comparative Example 7 | Comparative Example 2 | Comparative Example 8 | Comparative Example 9 |
|---|---|---|---|---|---|---|
| Adhesive Layer Composition [Parts by Mass] | | | | | | |
| Ropinirole Hydrochloride (In Terms of Free Form) | 10 (8.8) | 10 (8.8) | 10 (8.8) | 10 (8.8) | 10 (8.8) | 10 (8.8) |
| Sodium Hydroxide (Mol/Ropinirole Free Form) | 1.08 (0.8) | — | — | — | — | — |
| Sodium Hydrogen Carbonate (Mol/Ropinirole Free Form) | — | 1.42 (0.5) | 2.12 (0.75) | 2.83 (1.0) | 4.25 (1.5) | 5.66 (2.0) |
| Rubber-Based Adhesive Base Composition | 88.92 | 88.58 | 87.88 | 87.17 | 85.75 | 84.34 |
| Total | 100 | 100 | 100 | 100 | 100 | 100 |
| Skin Permeability | | | | | | |
| Relative Accumulated Permeation Rate [%] | 100 | 87.02 | 97.62 | 86.90 | 103.19 | 105.20 |

TABLE 3

|  | Comparative Example 1 | Example 2 | Example 3 | Example 4 | Example 5 | Example 6 |
|---|---|---|---|---|---|---|
| Adhesive Layer Composition [Parts by Mass] | | | | | | |
| Ropinirole Hydrochloride (In Terms of Free Form) | 10 (8.8) | 10 (8.8) | 10 (8.8) | 10 (8.8) | 10 (8.8) | 10 (8.8) |
| Sodium Hydroxide (Mol/Ropinirole Free Form) | 1.08 (0.8) | — | — | — | — | — |
| Potassium Hydrogen Carbonate (Mol/Ropinirole Free Form) | — | 1.69 (0.5) | 2.53 (0.75) | 3.37 (1.0) | 5.06 (1.5) | 6.75 (2.0) |
| Rubber-Based Adhesive Base Composition | 88.92 | 88.31 | 87.47 | 86.63 | 84.94 | 83.25 |
| Total | 100 | 100 | 100 | 100 | 100 | 100 |
| Skin Permeability | | | | | | |
| Relative Accumulated Permeation Rate [%] | 100 | 80.53 | 103.28 | 117.67 | 111.52 | 105.24 |

As is clear from the results shown in Table 2 to 3, the patches of the present invention obtained by using potassium hydrogen carbonate (Examples 2 to 6) were confirmed to have an excellent skin permeability to a degree equal to or more than the case of using sodium hydroxide (Comparative Example 1) and the case of using sodium hydrogen carbonate (Comparative Examples 2 and 6 to 9). Note that the same results were confirmed when the skin permeation test was also carried out on the patches obtained in the same manner as those of Examples 2 to 6 except that the rubber-based adhesive base composition was replaced with a silicone-based adhesive.

Next, Table 4 to 6 show the results obtained by carrying out the crystal precipitation evaluation test on the patches obtained in Comparative Examples 1, 2, and 8 to 11 and Examples 4 to 13 together with the compositions of the adhesive layer compositions (excluding the solvent).

TABLE 4

|  | Comparative Example 1 | Comparative Example 2 | Comparative Example 8 | Comparative Example 9 | Comparative Example 10 | Comparative Example 11 |
|---|---|---|---|---|---|---|
| Adhesive Layer Composition [Parts by Mass] | | | | | | |
| Ropinirole Hydrochloride (In Terms of Free Form) | 10 (8.8) | 10 (8.8) | 10 (8.8) | 10 (8.8) | 10 (8.8) | 10 (8.8) |
| Sodium Hydroxide (Mol/Ropinirole Free Form) | 1.08 (0.8) | — | — | — | — | — |

TABLE 4-continued

|  | Comparative Example 1 | Comparative Example 2 | Comparative Example 8 | Comparative Example 9 | Comparative Example 10 | Comparative Example 11 |
|---|---|---|---|---|---|---|
| Sodium Hydrogen Carbonate (Mol/Ropinirole Free Form) | — | 2.83 (1.0) | 4.25 (1.5) | 5.66 (2.0) | 7.08 (2.5) | 8.49 (3.0) |
| Rubber-Based Adhesive Base Composition | 88.92 | 87.17 | 85.75 | 84.34 | 82.92 | 81.51 |
| Total | 100 | 100 | 100 | 100 | 100 | 100 |
| Skin Permeability |  |  |  |  |  |  |
| Crystal Precipitation Evaluation | B | B | B | B | B | B |

TABLE 5

|  | Example 4 | Example 5 | Example 6 | Example 7 | Example 8 |
|---|---|---|---|---|---|
| Adhesive Layer Composition [Parts by Mass] |  |  |  |  |  |
| Ropinirole Hydrochloride (In Terms of Free Form) | 10 (8.8) | 10 (8.8) | 10 (8.8) | 10 (8.8) | 10 (8.8) |
| Potassium Hydrogen Carbonate (Mol/Ropinirole Free Form) | 3.37 (1.0) | 5.06 (1.5) | 6.75 (2.0) | 8.43 (2.5) | 10.11 (3.0) |
| Rubber-Based Adhesive Base Composition | 86.63 | 84.94 | 83.25 | 81.57 | 79.89 |
| Total | 100 | 100 | 100 | 100 | 100 |
| Crystal Precipitation Evaluation | A | A | A | A | A |

TABLE 6

|  | Example 9 | Example 10 | Example 11 | Example 12 | Example 13 |
|---|---|---|---|---|---|
| Adhesive Layer Composition [Parts by Mass] |  |  |  |  |  |
| Ropinirole Hydrochloride (In Terms of Free Form) | 15 (13.2) | 15 (13.2) | 15 (13.2) | 15 (13.2) | 15 (13.2) |
| Potassium Hydrogen Carbonate (Mol/Ropinirole Free Form) | 5.06 (1.0) | 7.59 (1.5) | 10.12 (2.0) | 12.65 (2.5) | 15.18 (3.0) |
| Rubber-Based Adhesive Base Composition | 79.94 | 77.41 | 74.88 | 72.35 | 69.82 |
| Total | 100 | 100 | 100 | 100 | 100 |
| Crystal Precipitation Evaluation | A | A | A | A | A |

As is clear from the results shown in Table 4 to 6, crystal precipitation was observed after the passage of a long period of time following manufacture in the case of using sodium hydroxide (Comparative Example 1) and in the case of sodium hydrogen carbonate, an alkali metal bicarbonate like potassium hydrogen carbonate (Comparative Examples 2 and 8 to 11), whereas the crystal precipitation was confirmed to be suppressed for the patches of the present invention obtained by using potassium hydrogen carbonate (Examples 4 to 13). Note that no difference was observed in the surface state of patch adhesive layer after 21-day storage for the three patches prepared in each of Comparative Examples 1, 2, and 8 to 11 and Examples 4 to 13, and the evaluation results are shown in Table 4 to 6. In addition, Raman spectrum measurement was carried out on the patch of Comparative Example 1 in which crystal precipitation was observed, and it was confirmed that the crystals precipitated were the crystals of ropinirole free form. The same results were confirmed when the crystal precipitation evaluation test was also carried out on the patches obtained in the same manner as those of Examples 4 to 13 except that the rubber-based adhesive base composition was replaced with a silicone-based adhesive.

Next, Table 7 shows the results obtained by carrying out the preparation suitability evaluation test on the patches obtained in Comparative Examples 12 and 13 and Example 14 together with the compositions of the adhesive layer compositions (excluding the solvent).

TABLE 7

|  | Comparative Example 12 | Comparative Example 13 | Comparative Example 14 |
|---|---|---|---|
| Adhesive Layer Composition [Parts by Mass] |  |  |  |
| Ropinirole Hydrochloride (In Terms of Free Form) | 20 (17.6) | 20 (17.6) | 20 (17.6) |
| Sodium Hydroxide | 2.70 | — | — |

TABLE 7-continued

|  | Comparative Example 12 | Comparative Example 13 | Comparative Example 14 |
|---|---|---|---|
| (Mol/Ropinirole Free Form) | (1.0) |  |  |
| Potassium Hydroxide (Mol/Ropinirole Free Form) | — | 3.78 (1.0) | — |
| Potassium Hydrogen Carbonate (Mol/Ropinirole Free Form) | — | — | 6.75 (1.0) |
| Rubber-Based Adhesive Base Composition | 77.30 | 76.22 | 73.25 |
| Total | 100 | 100 | 100 |
| Preparation Suitability Evaluation | A | C | A |

As is clear from the results shown in Table 7, the patch of the present invention obtained by using potassium hydrogen carbonate (Example 14) was confirmed to have an excellent preparation suitability. On the other hand, in the case of using potassium hydroxide, a potassium compound like potassium hydrogen carbonate (Comparative Example 13), an anchoring failure occurred between the adhesive layer and the backing layer to produce a preparation suitability evaluation of C, and it was confirmed that use as a preparation was difficult.

INDUSTRIAL APPLICABILITY

As described above, the present invention makes it possible to provide a patch which is excellent in skin permeability of ropinirole and which sufficiently suppresses crystal precipitation in the adhesive layer for a long period of time, and a package thereof.

The invention claimed is:

1. A patch comprising:
    a backing layer; and
    an adhesive layer, wherein
    the adhesive layer contains potassium hydrogen carbonate, and
    at least one selected from the group consisting of a ropinirole free form obtainable as a reaction product between a pharmaceutically acceptable acid addition salt of ropinirole and potassium hydrogen carbonate, and the pharmaceutically acceptable acid addition salt of ropinirole which remained unreacted,
    wherein
    a content of potassium hydrogen carbonate and/or a potassium hydrogen carbonate-derived component obtainable as a reaction product between the pharmaceutically acceptable acid addition salt of ropinirole and potassium hydrogen carbonate in terms of potassium hydrogen carbonate is 1.0 to 2.5 moles relative to a content of 1.0 mole of ropinirole and/or the pharmaceutically acceptable acid addition salt thereof in terms of ropinirole free form, the potassium hydrogen carbonate-derived component being selected from the group consisting of carbon dioxide gas ($CO_2$), carbonate ions ($CO_3^{2-}$), hydrogen carbonate ions ($HCO_3^-$), potassium ions ($K^+$), potassium salts, and mixtures thereof, and
    the adhesive layer contains rubber-based adhesives.

2. The patch according to claim 1, wherein the mixture further contains the potassium hydrogen carbonate-derived component.

3. The patch according to claim 1, wherein
    a content of ropinirole and/or the pharmaceutically acceptable acid addition salt thereof in terms of ropinirole free form is 7.7 to 20.0% by mass relative to a total mass of the adhesive layer.

4. A package comprising the patch according to claim 1 enclosed in a packaging container.

* * * * *

UNITED STATES PATENT AND TRADEMARK OFFICE
CERTIFICATE OF CORRECTION

PATENT NO. : 11,364,207 B2
APPLICATION NO. : 16/483511
DATED : June 21, 2022
INVENTOR(S) : Hideaki Ohashi et al.

It is certified that error appears in the above-identified patent and that said Letters Patent is hereby corrected as shown below:

In the Specification

Column 16, Table 7, Lines 59-60, please change "Comparative Example 14" to --Example 14-- as shown below Column 17, Table 7, Lines 3-4, please change "Comparative Example 14" to --Example 14-- as shown below Table 7

|  | Comparative Example 12 | Comparative Example 13 | Example 14 |
|---|---|---|---|
| Adhesive Layer Composition [Parts by Mass] | | | |
| Ropinirole Hydrochloride (In Terms of Free Form) | 20 (17.6) | 20 (17.6) | 20 (17.6) |
| Sodium Hydroxide (Mol/Ropinirole Free Form) | 2.70 (1.0) | - | - |
| Potassium Hydroxide (Mol/Ropinirole Free Form) | - | 3.78 (1.0) | - |
| Potassium Hydrogen Carbonate (Mol/Ropinirole Free Form) | - | - | 6.75 (1.0) |
| Rubber-Based Adhesive Base Composition | 77.30 | 76.22 | 73.25 |
| Total | 100 | 100 | 100 |
| Preparation Suitability Evaluation | A | C | A |

Signed and Sealed this
Ninth Day of April, 2024

Katherine Kelly Vidal
*Director of the United States Patent and Trademark Office*